(12) United States Patent
Ichihara et al.

(10) Patent No.: US 8,342,028 B2
(45) Date of Patent: Jan. 1, 2013

(54) PHOTOACOUSTIC MEASUREMENT APPARATUS

(75) Inventors: Shigeru Ichihara, Tokyo (JP); Takahiro Masumura, Tucson, AZ (US); Shuichi Kobayashi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 298 days.

(21) Appl. No.: 12/816,571

(22) Filed: Jun. 16, 2010

(65) Prior Publication Data
US 2010/0319453 A1 Dec. 23, 2010

(30) Foreign Application Priority Data
Jun. 23, 2009 (JP) ................................. 2009-148485

(51) Int. Cl.
*G01N 21/00* (2006.01)
*G01N 29/00* (2006.01)
(52) U.S. Cl. .............................. 73/643; 73/596; 356/432
(58) Field of Classification Search .................... 73/643, 73/596, 655, 657; 356/432
See application file for complete search history.

(56) References Cited

U.S. PATENT DOCUMENTS

| | | | | | |
|---|---|---|---|---|---|
| 4,551,018 | A | * | 11/1985 | Mannava et al. | 356/28.5 |
| 5,348,002 | A | * | 9/1994 | Caro | 600/310 |
| 5,363,220 | A | * | 11/1994 | Kuwayama et al. | 359/3 |
| 6,403,944 | B1 | * | 6/2002 | MacKenzie et al. | 250/214.1 |
| 6,786,099 | B2 | * | 9/2004 | Janik | 73/655 |
| 7,154,083 | B2 | * | 12/2006 | Mizuno | 250/234 |
| 7,586,611 | B2 | * | 9/2009 | Lowney et al. | 356/432 |
| 7,710,566 | B2 | * | 5/2010 | Arnott et al. | 356/432 |
| 2006/0184042 | A1 | | 8/2006 | Wang et al. | 600/476 |
| 2009/0066949 | A1 | | 3/2009 | Masumura | 356/326 |
| 2009/0069653 | A1 | | 3/2009 | Yoshida et al. | 600/323 |
| 2009/0069674 | A1 | | 3/2009 | Masumura et al. | 600/425 |
| 2009/0069685 | A1 | | 3/2009 | Nishihara et al. | 600/443 |
| 2010/0058870 | A1 | | 3/2010 | Kobayashi | 73/596 |
| 2010/0069750 | A1 | | 3/2010 | Masumura | 600/437 |
| 2010/0070233 | A1 | | 3/2010 | Masumura | 702/127 |
| 2012/0133941 | A1 | * | 5/2012 | Nakajima et al. | 356/432 |

FOREIGN PATENT DOCUMENTS

| | | |
|---|---|---|
| JP | H09-257755 | 10/1997 |
| JP | H10-000189 | 1/1998 |
| JP | 2009-204424 | 9/2009 |

* cited by examiner

*Primary Examiner* — J M Saint Surin
(74) *Attorney, Agent, or Firm* — Fitzpatrick, Cella, Harper & Scinto

(57) ABSTRACT

Disclosed is a photoacoustic measurement apparatus that irradiates a light beam onto a subject, from a same side as that of an acoustic wave detector, and that measures photoacoustic waves. The photoacoustic measurement apparatus has: an acoustic wave detector; a diffraction grating member provided in front of a detection surface of the detector; a light source that generates a light beam; and an optical system that guides the light beam from the light source towards the diffraction grating member. The diffraction grating member is configured such that the light beam led to the diffraction grating member is outputted by the diffraction grating member towards a subject surface that opposes the detection surface of the detector. As a result, light beams can strike a biological body in a near-perpendicular angle. This affords greater illumination efficiency, and allows light of substantial light energy to be irradiated deep inside biological structures.

5 Claims, 7 Drawing Sheets

FIG. 1A    WITHOUT DIFFRACTION GRATING
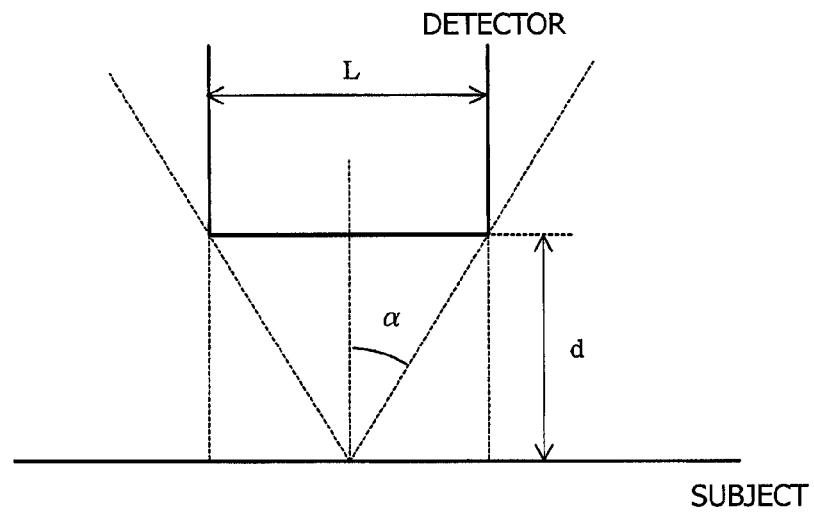
FIG. 1B    WITH DIFFRACTION GRATING
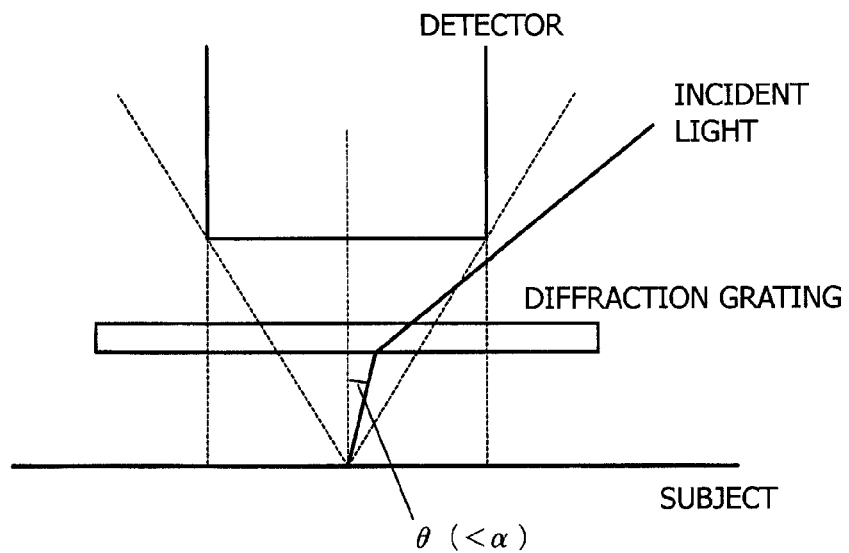

PHOTOACOUSTIC MEASUREMENT APPARATUS

BACKGROUND OF THE INVENTION

1. Field of the Invention

The present invention relates to a photoacoustic measurement apparatus that measures biological information on the basis of the photoacoustic effect.

2. Description of the Related Art

Ongoing research and development is being conducted on technologies for non-invasive visualization of biological information using high-transmittance near-infrared light. Biological constituent elements, such as water, fats, hemoglobin in blood vessels and so forth have characteristic spectra in the near-infrared wavelength band. Therefore, attention is being given to research aimed at obtaining functional information in-vivo through visualization of the spatial distribution of absorption coefficients from the above constituent elements.

The photoacoustic effect is a phenomenon whereby an object generates acoustic waves (typically, ultrasonic waves) when irradiated with pulsed light. These acoustic waves arise from volume expansion at regions that have a high absorption coefficient, within the subject to be measured. A photoacoustic measurement apparatus detects and reconstructs the generated acoustic waves by way of an acoustic wave detector. The spatial distribution of the absorption coefficients can be displayed as a result. Compared to light, acoustic waves have higher penetration into a biological body, and hence photoacoustic measurement apparatuses that rely on acoustic wave detection boast high spatial resolving power. In the present invention, the term "photoacoustic wave" denotes acoustic waves generated on account of volume expansion as a result of pulsed light irradiation.

Imaging equipment that exploits the photoacoustic effect includes, for instance, the device set forth in US Patent Application Publication No. 2006/0184042, which discloses a photoacoustic microscope that detects photoacoustic waves with high resolving power, by arranging a light source and an acoustic wave detector on a same side of a biological body. Light is irradiated in oblique incidence, from a side of the acoustic wave detector, in order to concentrate light in a region within the biological body.

SUMMARY OF THE INVENTION

In the apparatus set forth in US Patent Application Publication No. 2006/0184042, light beams are concentrated in a region located about several mm deep within a subject (biological body). The apparatus is suitable thus for imaging, with high resolving power, biological constituent elements that are present in the illuminated region. However, the light beams strike the subject obliquely, which translates into lower illumination efficiency. Preferably, the deep inside of the biological body is irradiated with as large a light energy as possible, with a view to obtaining photoacoustic waves from the deep portions of the subject.

Such being the case, it is an object of the present invention to provide a photoacoustic measurement apparatus that allows applying greater light energy into deep portions of a subject.

One aspect of the present invention provides a photoacoustic measurement apparatus that irradiates a light beam onto a subject, from a same side as that of an acoustic wave detector, and that measures photoacoustic waves. The apparatus includes: an acoustic wave detector; a diffraction grating member provided in front of a detection surface of the acoustic wave detector; a light source that generates a light beam; and an optical system that guides the light beam from the light source towards the diffraction grating member. And the diffraction grating member is configured such that the light beam led to the diffraction grating member is outputted by the diffraction grating member towards a subject surface that opposes the detection surface of the acoustic wave detector.

The present invention allows irradiating a light beam substantially perpendicularly onto a subject during measurement of the subject by bringing an acoustic wave detector into contact with, or close to, the subject. The present invention enables therefore more light energy to propagate down to deep portions of the subject, and to obtain larger acoustic waves from the deep portions of the subject.

Further features of the present invention will become apparent from the following description of exemplary embodiments with reference to the attached drawings.

BRIEF DESCRIPTION OF THE DRAWINGS

FIGS. 1A and 1B are diagrams for explaining the incidence angle of incident light onto a subject;

DESCRIPTION OF THE EMBODIMENTS

Figure 2A:
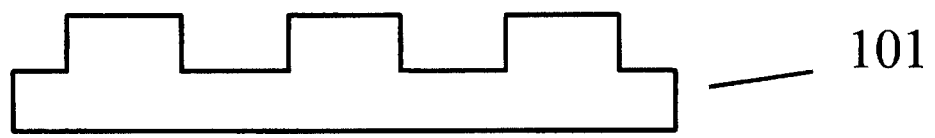
FIGS. 2A to 2C are schematic diagrams illustrating shapes of diffraction gratings.

Substantial amounts of light energy must propagate through deep inside the biological body in order for large photoacoustic waves to be acquired from absorbing bodies that are present deep inside the biological body. In order to cause light energy to propagate effectively down to deep portions, a light beam is preferably irradiated substantially perpendicularly to the biological body surface. The relationship between the irradiation angle of a light beam onto the biological body surface and illumination efficiency is illustrated next. The path traveled by a light beam that penetrates into a biological body is modified on account of the strong diffusive action of the biological body's interior. The penetration depth of the light beam varies thus depending on the incidence angle. Here, it is considered how the incident angle of a light beam onto the biological body affects penetration, assuming that the biological body is a uniform diffusive body having typical optical coefficients for biological bodies (diffusion coefficient $\mu s = 10 \text{ cm}^{-1}$, effective diffuse attenuation coefficient $\mu s' = 1 \text{ cm}^{-1}$, absorption coefficient $\mu a = 0.1 \text{ cm}^{-1}$). Ray tracing using Monte Carlo simulation was performed to estimate the amount of reaching light energy as a function of depth into the body. The amount of reaching light energy decreases substantially monotonously as the incidence angle increases, from depths of 5 to 30 mm from the irradiation surface. The amount of reaching light energy is of about 0.95 for an incidence angle of 20°, of about 0.87 for an incidence angle of 30° and of about 0.78 for an incidence angle of 40°, normalized to the amount of reaching light energy for an incidence angle of 0 degrees. Thus, the incidence angle of the light beam is preferably equal to or smaller than 40°, more preferably equal to or smaller than 20°, and yet more preferably 0° (perpendicular incidence). The depth reached by light is deepest for normal incidence.

As used in the present invention, the term "light beam" denotes a pencil of light rays emitted by a light source, and includes conceptually also a pencil of light rays reflected and/or transmitted by a diffraction grating. Herein, a light ray reflected and/or transmitted at a given site of a diffraction grating, and a light ray reflected and/or transmitted at another site of the diffraction grating, may travel along dissimilar directions, depending on the surface profile of the diffraction grating (the arrows in FIG. 5 and FIG. 6 denote light beams).

As used in the present invention, the term "light irradiation region" denotes a region struck by a light beam that is irradiated from a light source, from among the sites at which the photoacoustic measurement apparatus can come into contact with the subject during measurement. When a flat plate is used for fixing the subject, the light irradiation region denotes the irradiation region of the light beam at the position of the flat plate that can come into contact with the subject. If an acoustic matching layer such as a water bag is provided, the light irradiation region denotes an irradiation region on the acoustic matching layer.

Light irradiation is not limited to perfect normal incidence for all light beams, on account of imperfect coherence and beam divergence of the light source actually used, and on account also of the fact that the optical members are not ideal. With these angular fluctuation factors in mind, thus, normal incidence is defined in the present invention as an instance where the center of the incidence angle range is 0°.

Preferably, the light irradiation region is set at a region immediately below the acoustic wave detector, in order for light energy to reach deeper into the biological body. In a photoacoustic biological measurement apparatus (photoacoustic measurement apparatus) in which the acoustic wave detector and the light source are disposed on a same side, the structural constraints imposed by the acoustic wave detector mandate that the light source be arranged so as to avoid the acoustic wave detector. As a result, the light beams fail to strike the biological body directly and perpendicularly. Other constraints include a reduction in the photoacoustic waves that are detected by the acoustic wave detector in a case where light beams are irradiated perpendicularly, and it is the acoustic wave detector that is disposed so as to avoid the propagation path of the light beam. Such being the case, the present invention is configured in such a manner that a diffraction grating member that lets acoustic waves through and that has a light beam angle control section is disposed between the acoustic wave detector and the light irradiation region (i.e. the diffraction grating member is provided in front of the detection surface of the acoustic wave detector). An optical system is provided for guiding light from the light source towards the diffraction grating member. The diffraction grating member has a finely textured structure configured in such a manner that the outputted diffracted light strikes the subject surface opposite the detection surface. The outputted diffracted light is preferably near perpendicular, more preferably perpendicular, to the detection surface of the acoustic wave detector. In the above configuration, the propagation paths of the irradiated light beam and of the photoacoustic waves are overlapped, thanks to which a light beam can be irradiated perpendicularly to the biological body. The light beam can propagate thus down to deep portions of the biological body. The light beam irradiation position and the detection position of the acoustic wave detector are close to each other. As a result, the acoustic waves are little attenuated, and photoacoustic waves from deep inside the biological body can be detected with good sensitivity. When the incidence angle of the light beam that strikes the diffraction grating member varies with the position, the textured structure of the diffraction grating member is preferably modified in accordance with the incidence angle of the light beam. Diffracted light can strike thereby the biological body perpendicularly, even for a varying incidence angle of the light beam. In the present invention, the "detection surface" of the acoustic wave detector is the surface that opposes the subject during measurement, and at which there is disposed an element for detecting photoacoustic waves and converting the latter into electric signals.

In the present invention, the "incidence angle of the light beam" denotes the angle ($\theta$) formed by the light beam and the normal of the light irradiation region. When no diffraction grating member is provided, and light is irradiated onto the light irradiation region that is disposed immediately below the acoustic wave detector, the incidence angle of the light beam must be at least $\alpha$ degrees, such as the one illustrated in FIG. 1A. The incidence angle of the light beam is constrained herein by the size of the acoustic wave detector. Although arranging a diffraction grating member is a characteristic feature of the present invention, the latter is not limited to an instance in which the light beam is perpendicular to the light irradiation region. In the present invention, preferably, the incidence angle of the light beam (angle $\theta$ in FIG. 1B) is made smaller than the above $\alpha$ degrees, by providing the diffraction grating member. In the present invention, thus, the diffraction grating member is arranged such that the reflected and/or diffracted light beams have an incidence angle smaller than $\alpha$ degrees. Deeper portions of the subject can be irradiated thus through the arrangement of the diffraction grating member.

Figure 7:
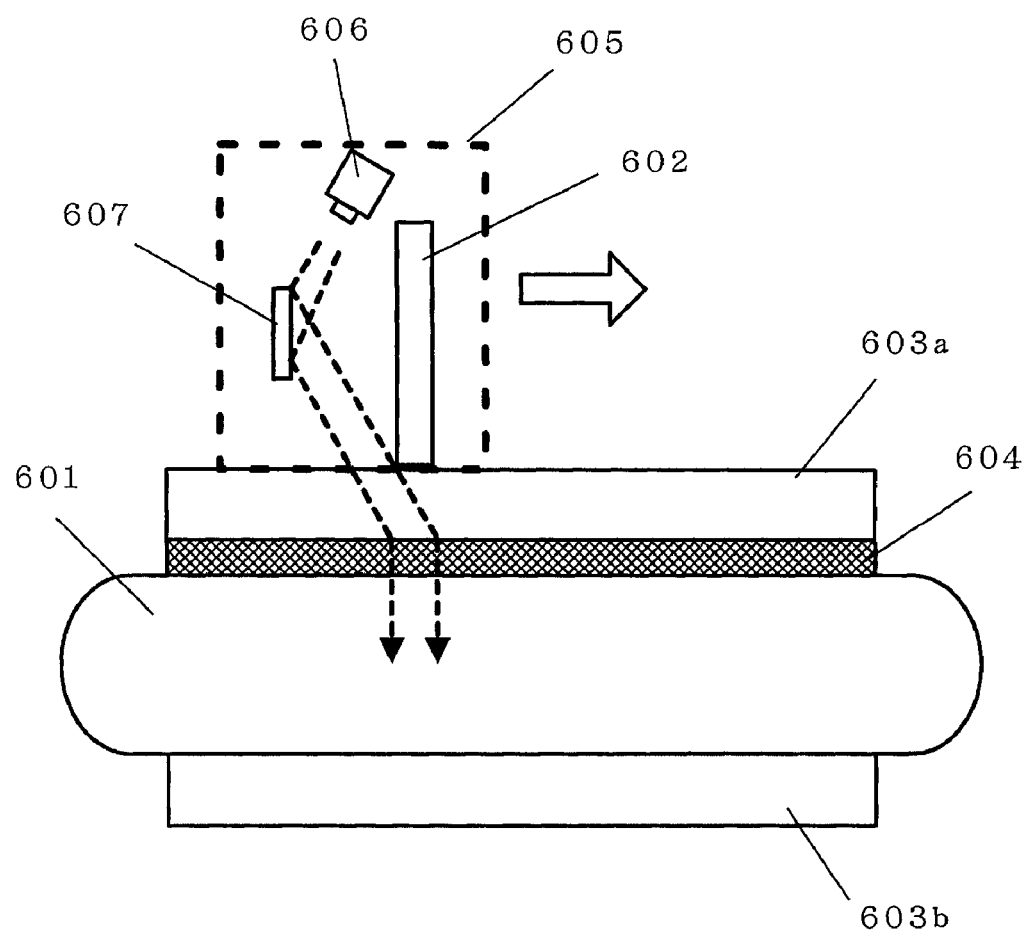
FIG. 7 is a schematic diagram of a fourth embodiment of the present invention.

The incidence angle $\alpha$ of the light beam depends on the acoustic wave detector size L (corresponding to the length of the short side, for a rectangular shape, and the length of the diameter, for a circular shape) and on the distance d from the subject up to the detection surface, as illustrated in FIG. 1A. The incidence angle $\alpha$ is greater, in particular, in a case where there is used a two-dimensional acoustic wave detector (2D probe with elements arrayed in two dimensions) for 3D imaging. A standoff for acoustic matching and a parallel plate as illustrated in FIG. 7 may be provided between the subject and the acoustic wave detector, and thus the light irradiation region is made to be immediately below the acoustic wave detector. The acoustic wave detector size L may range from the length of the short side of an ordinarily used 1D probe to the size of a 2D probe. The incidence angle $\alpha$, although depending on the distance d, is near perpendicular to the detector surface when the size L is of about several mm, as in the case of a 1D probe. As a result, the depth into the biological body that is reached by the light energy does not vary substantially on account of the presence or absence of the diffraction grating. When the size L is equal to or greater than about 10 mm, however, the incidence angle of the light beam becomes substantial, of 45 degrees, even if the distance d is small, of about 5 mm. The effect of inserting the diffraction grating is therefore distinctive in this case. The effect of inserting the diffraction grating is thus distinctive when L/2 d, which is the tangent $\tan \alpha$ of the incidence angle $\alpha$, is equal to or greater than about 0.364, which corresponds to an incidence angle of 20°, and further when $\tan \alpha$ is equal to or greater than 0.84, which corresponds to 40°. In this case, the incidence angle $\theta$ of the light beam that exits from the inserted diffraction grating, with respect to the subject surface, is preferably set so as to satisfy $\tan \theta < L/2\ d$. Such an incidence angle $\theta$ is not feasible in a case where the light beam is irradiated obliquely onto the subject in order to avoid the acoustic wave detector. Needless to say, the closer the incidence angle θ is to a perpendicular angle (θclose to zero), the more preferable the angle is.

The diffraction grating member is provided on the propagation path of the acoustic waves, and hence the diffraction grating member is preferably transmissive to acoustic waves. A diffraction grating member that transmits acoustic waves is a member that does not significantly attenuate the transmitted acoustic waves. Regardless of whether the acoustic wave attenuation factor of the material is small, or, by contrast, the material does attenuate acoustic waves readily, the transmissivity of the diffraction grating towards acoustic waves can be ensured by configuring the diffraction grating using a member that is sufficiently thin relative to the wavelength of the acoustic waves. In the photoacoustic biological measurement apparatus of the present invention, the diffraction grating member can be disposed within an acoustic matching layer that is provided between the biological bodies and the acoustic wave detector. The acoustic impedance of biological bodies is close to the acoustic impedance of water, $1.5 \times 10^6$ kg·m$^{-2}$·s. The speed of sound in biological bodies is about 1500 m·s$^{-1}$. The frequency of the acoustic wave detector ranges from about 1 to 50 MHz, which is about 1.5 mm to 30 μm in terms of one wavelength. If a material having significant acoustic wave attenuation is used in the diffraction grating member, the transmissivity of the latter towards acoustic waves can be increased, regardless of the material used, by setting the thickness of the material to be equal to or smaller than 1/30 of the wavelength of the acoustic waves. Preferably, the thickness of the diffraction grating member is equal to or smaller than 1/30 of the wavelength of the acoustic waves, as a yardstick of transparency towards acoustic waves, but such a thickness is not a prerequisite. Although transmittance to acoustic waves decreases gradually when the thickness of the diffraction grating member is equal to or grater than 1/30, as described above, the thickness of the member may be equal to or greater than the thickness prescribed herein so long as that the intensity of the detection signal is sufficiently strong. One wavelength of acoustic waves having a frequency of 10 MHz measures about 150 μm in biological bodies. Therefore, the thickness of the diffracting optical element is preferably equal to or smaller than 5 μm. Transmittance to photoacoustic waves is preferably equal to or greater than 80%, more preferably equal to or greater than 90%.

Diffraction gratings are ordinarily used as spectroscopes for dividing light through diffraction, but in the present invention the diffraction grating is used as a means for controlling the angle of light beams. A single-wavelength pulsed laser having a wavelength that may range from the near-infrared to the visible region is used as the light source of the photoacoustic measurement apparatus. The diffraction grating is used thus for controlling the angle of a light beam having a specific wavelength. The diffraction grating member used may be a reflective-type or a transmissive-type diffraction grating member.

Figure 2B:
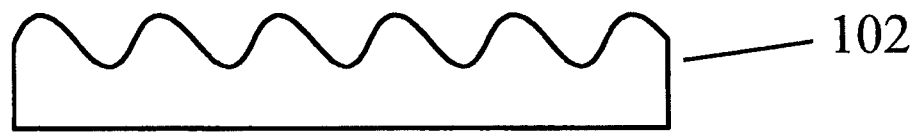
Figure 2C:

The cross-sectional shape of the diffraction grating may be, for instance, a square-wave shape 101, a sinusoidal shape 102 or a blazed (sawtooth) shape 103, as illustrated in FIGS. 2A to 2C.

The diffraction-efficiency peak wavelength of the square-wave shaped diffraction grating 101 is determined by the depth of the grooves and the duty ratio (groove width versus groove period). Ordinarily, the diffraction efficiency of even-order light is lower for square-wave shapes than that for sinusoidal shapes or blazed shapes. The texture of the diffraction grating is line symmetrical, and hence it does not concentrate diffracted light into a specific diffraction order.

The diffraction-efficiency peak wavelength of the sinusoidal diffraction grating 102 is determined by the depth of the grooves. The diffraction efficiency of the diffraction grating 102 is broad over a wide wavelength range. Ordinarily, the diffraction efficiency is about half that of a blazed diffraction grating, although high diffraction efficiency can be achieved if the ratio groove depth/groove period is large. The sinusoidal diffraction grating 102 is used in the near-infrared or in case of a wide wavelength range. However, the texture is line-symmetrical, as in the case of the square-wave shaped diffraction grating 101, and hence it does not concentrate diffracted light into a specific diffraction order.

Figure 3:
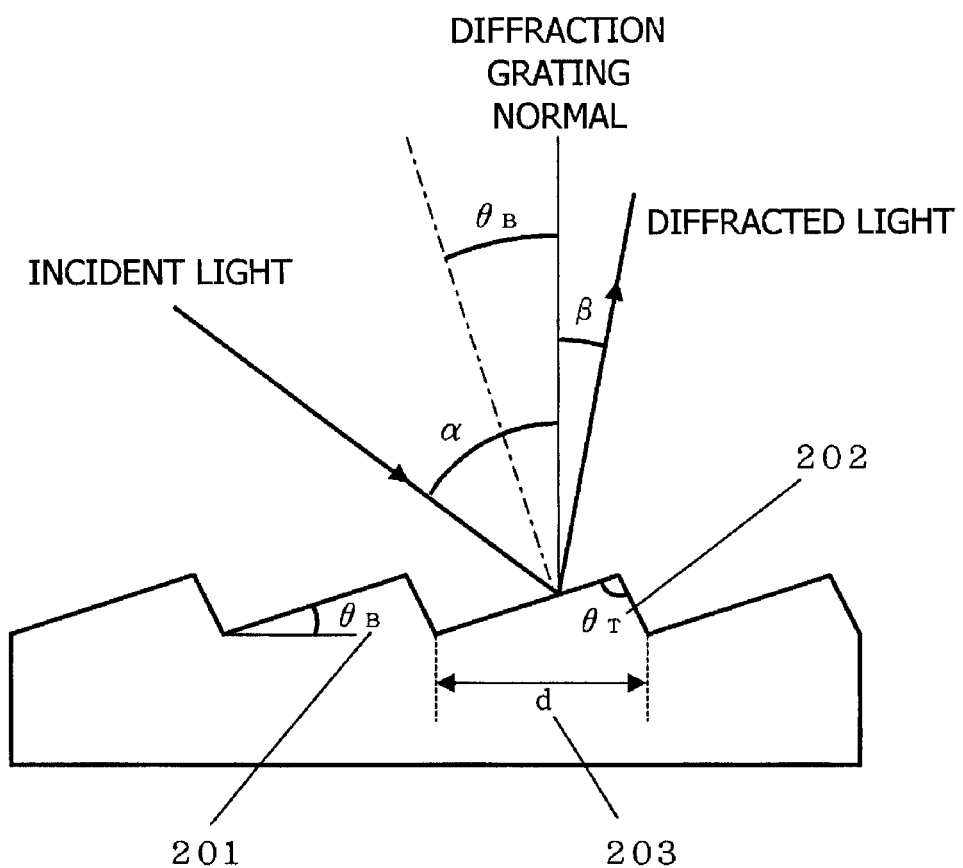
FIG. 3 is an explanatory diagram of diffraction in a reflective-type blazed diffraction grating.

Meanwhile, the below-described blaze wavelength ($\lambda$B: diffraction efficiency peak wavelength) of the blazed diffraction grating 103 is determined according to the incident light of a specific wavelength. The diffraction grating 103 exhibits thus high diffraction efficiency for specific wavelengths, mainly in the ultraviolet to the visible (and near-infrared) regions. The texture of the diffraction grating is herein line-asymmetrical, and diffracted light can be concentrated in specific wavelengths. As a result, a blazed diffraction grating is the optimal diffraction grating for the light-beam angle control section of the present invention. Such a blazed diffraction grating is explained below with reference to FIG. 3. The explanation below deals with an example of a reflective-type diffraction grating.

The grating equation is given by the relationship formula $$d(\sin \alpha \pm \sin \beta) = m\lambda \quad (1)$$

Herein, α denotes the incidence angle with respect to the normal of the diffraction grating, β denotes the angle of diffracted light, $\theta_B$ denotes the blaze angle, $\theta_T$ denotes the apex angle, and d denotes the grating pitch. In the explanation below the incidence angle is notated with respect to the above reference.

There are multiple diffraction orders m that satisfy the relationship formula (1), and hence the incident light of wavelength λ is divided into a plurality of diffracted light beams. In zero-order diffracted light (m=0), transfer holds α=β for the light that strikes the diffraction grating, regardless of the relationship between the wavelength λ and the grating period d. The same law applies herein as in a case of specular incidence and reflection. The sign in the left side of the relationship formula (1) is defined as positive for light diffracted on the side of the incident light, and negative for light diffracted on the opposite side of the incident light, with reference to the zero order. The blaze angle ($\theta_B$) is $$\theta_B = (\alpha + \beta)/2 \quad (2)$$

The wavelength is notated herein as the blaze wavelength ($\lambda_B$). Substituting formula (2) in formula (1), we obtain an expression for $\lambda_B$ $$\lambda_B = 2d/m \cdot \sin(\theta_B) \cdot \cos(\alpha - \theta_B) \quad (3)$$

In a blazed reflective-type diffraction grating, the greater part of the energy concentrates in m-order diffracted light when the incident light and the m-order diffracted light are in a specular reflection relationship. In order to maximize the light use efficiency in the diffraction grating, the geometry of the diffraction grating must be optimized at the used wavelength, in terms of, for instance, blaze angle with respect to the incidence angle, and also the diffraction efficiency (reflectance of first-order diffracted light) must be enhanced.

A characterizing feature of the present invention is that the diffracted light beam is perpendicular to the biological body surface, and the propagation path of the detected acoustic waves overlaps with the propagation path of the diffracted light beam that is irradiated onto the biological body. As a result, the angle β of the diffracted light is 0° when the diffraction grating is disposed parallel to the irradiated biological body surface. If the diffraction grating is disposed in a non-parallel attitude, then the angle of diffracted light is best adjusted in accordance with the tilt of the diffraction grating. A specific wavelength is used in the incident light, and the optimal incidence angle α and grating pitch d for the wavelength are determined relative to each other on the basis of relationship formula (1). According to relationship formula (2), the blaze angle $\theta_B$ depends on the incidence angle α. Preferably, the apex angle $\theta_T$ is such that the incident light onto the oblique face of the diffraction grating is not blocked, and such that the surface area of the irradiated oblique face is maximal. For example, for a light beam having an incidence angle of 60° and a wavelength of 800 nm, the diffraction grating used has preferably a grating pitch of 924 nm and a blaze angle of 30°. The incidence angle onto the diffraction grating is fixed in the illustrated example. However, normal incidence onto the biological body can also be achieved by controlling the diffraction angle, through modulation of the grating pitch and blaze angle in accordance with the incidence angle, in case where there is a variation in the incidence angle of the light beam that is irradiated onto the diffraction grating. The fine structure of the diffraction grating may be modulated to cope with a light beam having an incidence angle that, for instance, changes gradually from 50° to 70°. The grating pitch in this case is set to 1044 nm and the blaze angle to 25° at a position where the incidence angle is 50°, while the grating pitch is set to 851 nm and the blaze angle to 35° at a position where the incidence angle is 70°. The fine structure of the diffraction grating is caused to vary continuously for incidence angles in between. The intermediate fine structure may also be caused to vary stepwise.

In the reflective-type diffraction grating, the surface of the diffraction grating has deposited thereon a material having high resistance towards the incident light. The material, however, is not particularly limited, and there is ordinarily used a metallic thin film of Al, Au or the like having high reflectance. In particular, Au having high reflection efficiency is preferably used in the near-infrared region (700 to 1100 nm). Metallic materials have substantial acoustic wave attenuation (i.e. are materials that reflect acoustic waves). Therefore, the thickness of the metallic thin film is preferably of about several μm, so that the metallic thin film lets acoustic waves through.

Figure 4:
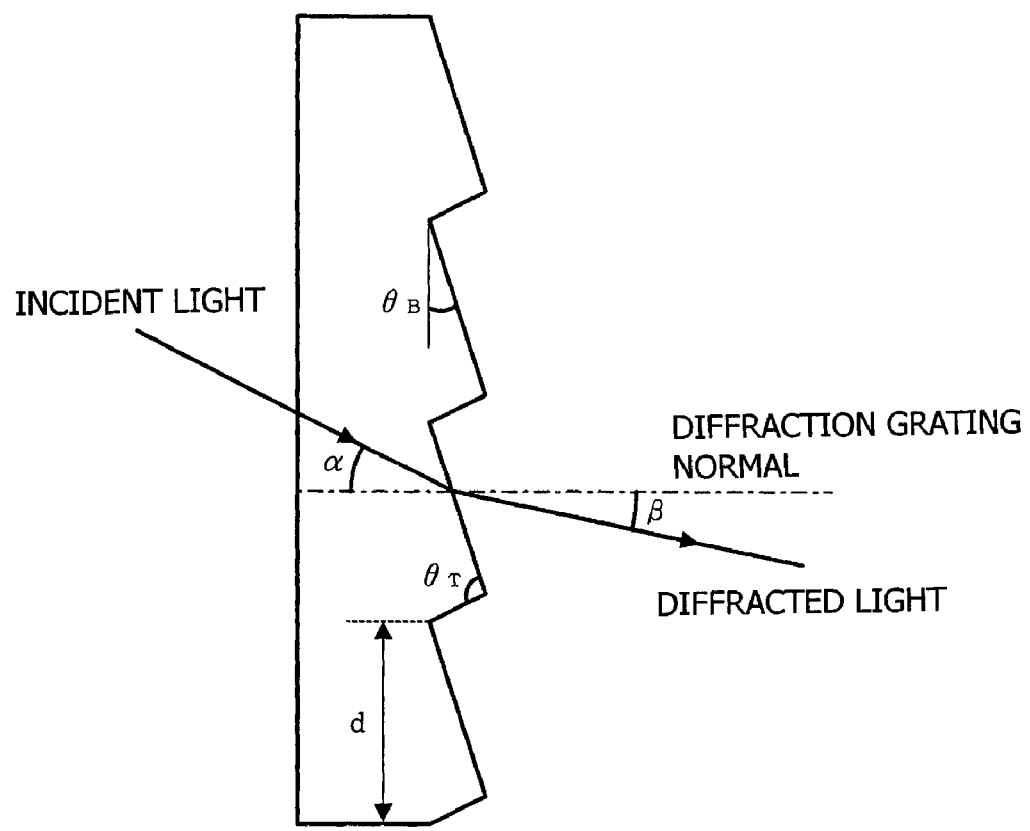
FIG. 4 is an explanatory diagram of diffraction in a transmissive-type blazed diffraction grating.

The grating equation given by the relationship formula (1) holds also for a transmissive-type diffraction grating, as in the case of a reflective type, but it should be noted that light is refracted on the oblique face of the diffraction grating, as illustrated in FIG. 4. Refraction obeys Snell's law, as follows:

$$n1 \cdot \sin(\theta_B + \alpha) = n2 \cdot \sin(\theta_B + \beta) \qquad (4)$$

Herein, n1 denotes the refractive index of the diffraction grating, n2 denotes the refractive index of an object on the exit side, and $\theta_B$ denotes the blaze angle. For example, a diffraction angle of 0° is obtained for an incidence angle of 20° through the use of a diffraction grating having a grating pitch of 867 nm and a blaze angle of 81.2°, in the case where the used wavelength is 800 nm, the refractive index of the resin is 1.5 and a biological body (having a putative refractive index of 1.33) is on the exit side. Similarly, for example, a diffraction angle of 0° is obtained for an incidence angle of 10° through the use of a diffraction grating having a grating pitch of 1159 nm and a blaze angle of 86.2°, in the case where the used wavelength is 800 nm, the refractive index of the resin is 1.5 and an acoustic wave matching layer having a refractive index of 1.46 is on the exit side.

Although a blazed diffraction grating is used in the explained examples, there is no limitation on the use, in the present invention, of a square-wave shaped or sinusoidal diffraction grating. The shape of a square or sinusoidal diffraction grating need only be also appropriately designed.

Example 1

Figure 5:
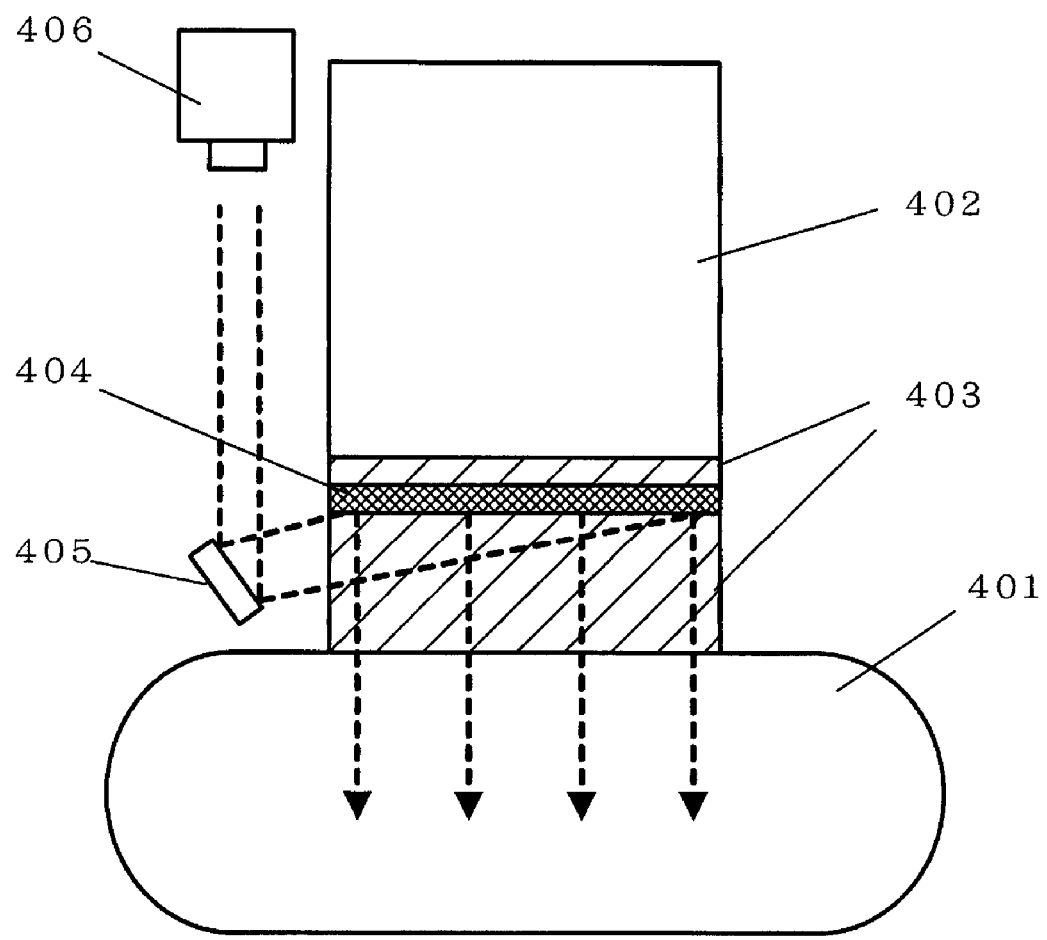
FIG. 5 is a schematic diagram of a first and a second embodiment of the present invention.

FIG. 5 illustrates a schematic diagram of a first example. A reflective-type diffraction grating is used as the diffraction grating. A subject 401 and the detection surface of an acoustic wave detector 402 are disposed facing each other substantially parallelly. An acoustic wave matching layer 403 of a solvent medium is provided in between, and a reflective-type blazed diffraction grating 404 is disposed, in the acoustic wave matching layer 403, so as to be substantially parallel to the acoustic wave detector 402. Light beams are irradiated by an external light source 406, onto the diffraction grating 404 from the side of the subject 401, by way of a mirror 405, so that diffracted light is irradiated onto the subject 401. The optical system has been omitted in the figure, except for the mirror 405. The transversal width of the detection surface of the acoustic wave detector used is 40 mm. The distance between the detection surface and the subject is 10 mm. The incidence angle of the light beam that strikes the diffraction grating 404 is 60° with respect to the normal direction to the subject. As the light source 406 there was used pulsed light having a wavelength of 800 nm, from a titanium sapphire (Ti:S) laser that used a neodymium YAG (Nd:YAG) laser, which is a nanosecond pulsed laser, as an excitation source. In order to irradiate diffracted light perpendicularly onto a biological body (perpendicularly to the detector) under these conditions, the blazed diffraction grating 404 is provided with a fine structure having a grating pitch 924 nm and a blaze angle 30°. The substrate used in the diffraction grating was a polymethylpentene resin having little acoustic wave attenuation. A reflective film, in the form of a 1 μm-thick Au coating, was used on the surface of the reflective-type diffraction grating. The center frequency band of the acoustic wave detector used was 7.5 MHz.

A known acoustic wave source and the acoustic wave detector of the present example were disposed facing each other inside a water tank, and the above-described diffraction grating was disposed in between. The change in intensity of acoustic waves was measured for a case where the diffraction grating was interposed and a case where it was not. The detection signal intensity remains virtually unchanged, regardless of the presence or absence of the diffraction grating. This indicates that the diffraction grating does not influence acoustic wave detection, if the thickness of the diffraction grating is sufficiently thin with respect to the wavelength of the acoustic wave. Under the above-described conditions, a phantom that simulated a biological body was used as the subject, an absorbing body having a diameter of 1 mm was disposed at a depth of 2 cm from the irradiation surface, and acoustic waves were acquired. The acquired acoustic waves yielded larger signals as compared with a case in which the subject surface was irradiated with oblique incidence and no diffraction grating was used.

Example 2

An explanation follows next on a second example of the present invention. Example 2 is substantially identical to Example 1 of the present invention, but herein the incidence angle of the light beams that strike the diffraction grating is caused to change gradually from 50° to 70° according to the site on the diffraction grating. The diffraction grating 404 used in the present example is a blazed reflective-type diffraction grating identical to that of Example 1, but with the structure of the diffraction grating (grating pitch and blaze angle) varying gradually. Specifically, the grating pitch is 1044 nm and the blaze angle is 25° at sites where the incidence angle of the light beam is 50°. The grating pitch is 924 nm and the blaze angle is 30° at sites where the incidence angle is 60°. The grating pitch is 851 nm and the blaze angle is 35° at sites where the incidence angle is 70°. The grating pitch and blaze angle of the diffraction grating are thus gradually modulated as described above. As in the case of Example 1, a phantom that simulated a biological body was used as the subject, an absorbing body having a diameter of 1 mm was disposed at a depth of 2 cm from the irradiation surface, and acoustic waves were acquired. The acquired acoustic waves yielded larger signals as compared with a case in which the subject surface was irradiated with oblique incidence and no diffraction grating was used.

Example 3

Figure 6:
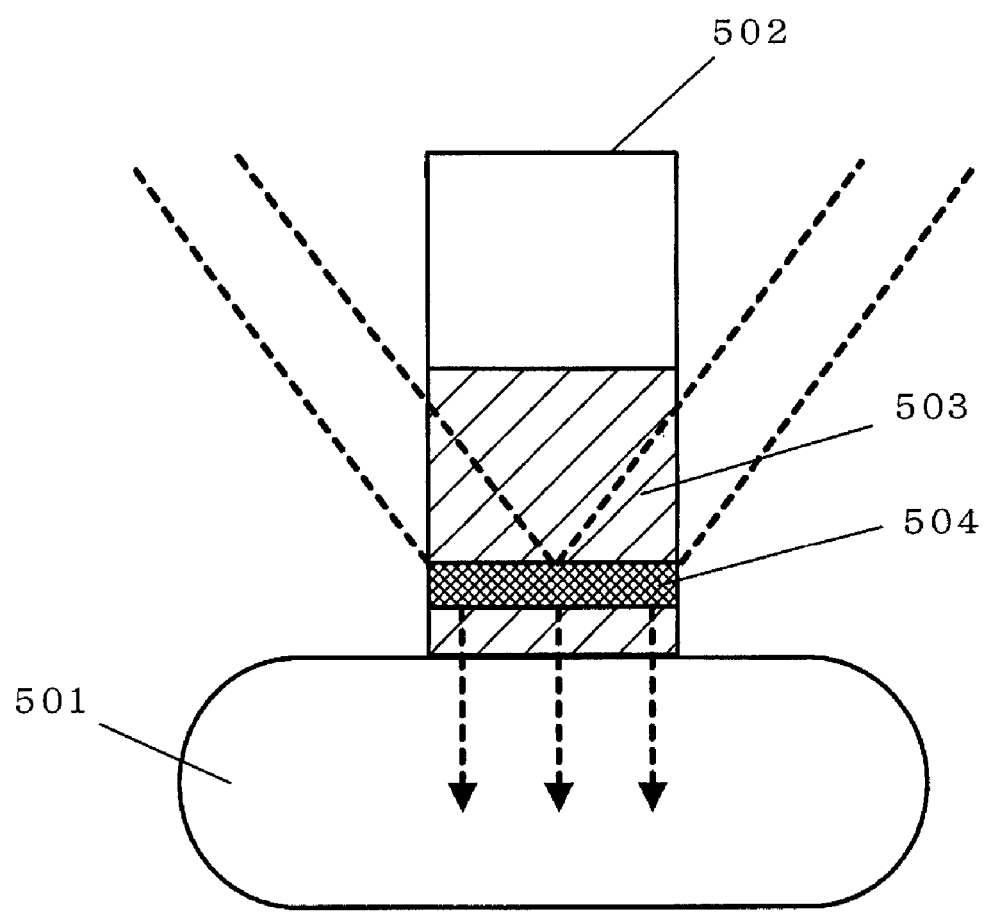
FIG. 6 is a schematic diagram of a third embodiment of the present invention.

FIG. 6 shows a schematic diagram of a third example according to the present invention. Unlike in Example 1, a transmissive-type diffraction grating is used herein as the diffraction grating. A subject 501 and the detection surface of an acoustic wave detector 502 are disposed facing each other substantially parallelly. An acoustic wave matching layer 503 of a solvent medium is provided in between, and a transmissive-type blazed diffraction grating 504 is disposed substantially parallel to the acoustic wave detector 502. The transversal width of the detection surface of the acoustic wave detector used is 10 mm. The distance between the detection surface and the subject is about 14 mm. Light beams from external light sources (not shown) are irradiated, by way of a lens, onto the diffraction grating, from the side of the acoustic wave detector 502, so that diffracted light is irradiated onto the subject 501. The light sources used are pulsed light having a wavelength of 800 nm, as in Example 1. In the present example, light beams from the light sources strike the diffraction grating 504 at an angle of 20° with respect to the normal direction of the subject, from both sides of the acoustic wave detector 502. The light beams irradiated from both sides coincide at the center of the diffraction grating 504. The refractive index of the acoustic wave matching layer 503 is 1.46. There is used a transmissive-type blazed diffraction grating 504 capable of irradiating diffracted light perpendicularly to a biological body under these conditions. The substrate used in the diffraction grating was a polymethylpentene resin having little acoustic wave attenuation. In case that the incidence angle of the light beam onto the diffraction grating 504 varies with the position, the structure of the diffraction grating 504 may also be modified in accordance with the position (incidence angle), in the same way as in Example 2. A phantom that simulated a biological body was used as the subject, under the above-described conditions. An absorbing body having a diameter of 1 mm was disposed at a depth of 2 cm from the irradiation surface, and acoustic waves were acquired. The acquired acoustic waves yielded larger signals as compared with a case in which the subject surface was irradiated with oblique incidence and no diffraction grating was used.

Example 4

FIG. 7 shows a schematic diagram of a fourth example according to the present invention. As in Example 3, a transmissive-type diffraction grating was used herein as the diffraction grating. In the present embodiment there are provided parallel plates 603a,b that sandwich a subject 601, in order to compress the subject so that the latter becomes parallel to the detection surface. The transmissive-type diffraction grating 604 is formed on the parallel plate 603a, on the side of the acoustic wave detector 602. The transversal width of the detection surface of the acoustic wave detector used is 10 mm. The distance between the detection surface and the subject is about 14 mm. The parallel plate 603a is irradiated by an external light source 606, so that the subject 601 is irradiated by way of the diffraction grating. The incidence angle onto the diffraction grating, by way of a mirror 607, is 20° with respect to the normal direction of the subject. The light source used is pulsed light having a wavelength of 800 nm, as in Example 1. In the present example, the refractive index of the parallel plate 603a used is 1.5. Under these conditions, the transmissive-type blazed diffraction grating 604 has a grating pitch of 867 nm and a blaze angle of 81.2°, so as to irradiate diffracted light perpendicularly to the biological body. In the present example, there is provided a scanning mechanism 605, in which the light source and the acoustic wave detector 602 are integrated together, that scans the parallel plate 603 in two dimensions. A phantom that simulated a biological body was used as the subject, under the above-described conditions. An absorbing body having a diameter of 1 mm was disposed at a depth of 2 cm from the irradiation surface, and acoustic waves were acquired. The acquired acoustic waves yielded larger signals as compared with a case in which the subject surface was irradiated with oblique incidence and no diffraction grating was used.

Example 5

An explanation follows next on a fifth example of the present invention. Example 5 is substantially identical to Example 1 of the present invention, but unlike Example 1, there is provided a blazed diffraction grating that irradiates diffracted light at 15° onto the detector. A phantom simulating a biological body was used as the subject. An absorbing body having a diameter of 1 mm was disposed at a depth of 2 cm from the irradiation surface, and acoustic waves were acquired. The result was compared with Example 1 and an instance in which no diffraction grating was disposed. The acquired acoustic waves were smaller than those in Example 1, but yielded larger signals as compared with the case in which the subject surface was irradiated with oblique incidence and no diffraction grating was used. A distinctive effect was found to be elicited through the use of a diffraction grating.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-148485, filed on Jun. 23, 2009, which is hereby incorporated by reference herein in its entirety.

What is claimed is:

1. A photoacoustic measurement apparatus that irradiates a subject with a light beam, from a same side as that of an acoustic wave detector, and that measures photoacoustic waves, the apparatus comprising:
   an acoustic wave detector;
   a diffraction grating member provided in front of a detection surface of said acoustic wave detector;

a light source that generates a light beam; and an optical system that guides the light beam from said light source towards said diffraction grating member, wherein said diffraction grating member is configured such that the light beam led to said diffraction grating member is outputted by said diffraction grating member towards a subject surface that opposes said detection surface of said acoustic wave detector, wherein the shape of said detection surface is rectangular or circular, and wherein said diffraction grating member is configured such that an incidence angle θ of the light beam outputted by said diffraction grating member with respect to the subject satisfies tan θ<L/2d, where L denotes a length of a short side or diameter of said detection surface, and d denotes a distance between said detection surface and a surface of contact with the subject.

2. The photoacoustic measurement apparatus according to claim 1, wherein said diffraction grating member is configured such that the light beam outputted by said diffraction grating member is perpendicular to said detection surface.

3. The photoacoustic measurement apparatus according to claim 1, wherein an incidence angle of the light beam that strikes said diffraction grating member varies in accordance with positions, and a structure of said diffraction grating member varies in accordance with the incidence angle of the light beam, with diffracted light outputted by said diffraction grating member being perpendicular to said detection surface of said acoustic wave detector.

4. The photoacoustic measurement apparatus according to claim 1, wherein said diffraction grating member is transmissive to acoustic waves.

5. The photoacoustic measurement apparatus according to claim 1, further comprising a flat plate that is disposed between said acoustic wave detector and the subject, and that compresses the subject parallelly to said detection surface of said acoustic wave detector, wherein said flat plate is said diffraction grating member.

* * * * *